United States Patent [19]

Poler

[11] Patent Number: 5,697,923
[45] Date of Patent: Dec. 16, 1997

[54] CORNEAL DRAPE FOR USE IN PERFORMING A PHOTOREFRACTORY KERATECTOMY PROCEDURE

[76] Inventor: Stanley Poler, 78 E. Second St., New York, N.Y. 10003

[21] Appl. No.: 412,523

[22] Filed: Mar. 29, 1995

[51] Int. Cl.$^6$ ............................................. A61B 17/36
[52] U.S. Cl. ............................................................. 606/4
[58] Field of Search .......................... 606/4, 5, 6, 10, 606/11, 12; 128/847, 849, 858; 604/294, 300, 302

[56] References Cited

U.S. PATENT DOCUMENTS

| | | | |
|---|---|---|---|
| 4,570,626 | 2/1986 | Norris et al. | 128/858 |
| 4,665,913 | 5/1987 | L'Esperance. | |
| 4,729,372 | 3/1988 | L'Esperance. | |
| 4,770,172 | 9/1988 | L'Esperance. | |
| 5,004,333 | 4/1991 | Bruhl, Jr. | 128/858 |
| 5,207,668 | 5/1993 | L'Esperance. | |
| 5,312,320 | 5/1994 | L'Esperance. | |
| 5,368,590 | 11/1994 | Itoh | 606/5 |
| 5,503,165 | 4/1996 | Schachar | 606/4 |
| 5,505,723 | 4/1996 | Muller | 606/5 |
| 5,507,740 | 4/1996 | O'Donnell, Jr. | 606/4 |

*Primary Examiner*—Jennifer Bahr
*Assistant Examiner*—Sonya Harris-Ogugua
*Attorney, Agent, or Firm*—Hopgood, Calimafde, Kalil & Judlowe

[57] ABSTRACT

The invention contemplates a template or mask for use in aid of a photorefractory keratectomy procedure for recurvature of a cornea. The template or mask is of flexible sheet material that is so fenestrated or otherwise configured as to be self-adherent to the cornea in the region outside of and surrounding the central optically used area of tissue-ablating recurvature, the template being configured to provide ready centering on the visual axis. The self-adherence is relative, intended only to serve for correct centering, and for moisture-retention, regardless of the corneal curvature to which it is applied.

25 Claims, 3 Drawing Sheets

CORNEAL DRAPE FOR USE IN PERFORMING A PHOTOREFRACTORY KERATECTOMY PROCEDURE

BACKGROUND OF THE INVENTION

The invention relates to the performance of surgery upon the anterior surface of the cornea, in order to change the anterior-surface profile and thereby change the optical performance of a given eye, via in vivo surgery.

Photorefractory keratectomy (PRK) is the term currently used to describe such a procedure, for the case of tissue-ablating energy delivered to the optically used central circular area of the anterior surface of the cornea, with such controlled pattern of energy fluence through a given procedural program of exposure to corneal tissue as to effect a sculpturing recurvature of the cornea, be it a myopia-reducing change, or a hyperopia-reducing change or an astigmatism-reducing change in the optical performance of the anterior surface of the cornea. L'Esperance, Jr. U.S. Pat. Nos. 4,665,913, 4,729,372, 4,770,172, 5,207,668, and 5,312,320 are illustrative of various of these techniques, which are within and illustrative of the available art, and therefore need not now be described. Argon-fluoride excimer lasers are commercially available for pulsed delivery of ultraviolet radiation at 290 nanometers (nm); these lasers are among the sources of radiant energy that are adapted for use in tissue-ablating cornea-sculpturing procedures.

One of the problems with laser surgery of the character indicated is that its focus of procedural impact on the cornea is local to the approximately 5-mm diameter, central, optically used circular area of the cornea. And even though the ablative surgery to accomplish a given corneal recurvature is performed in relatively short time, in the order of one minute or less, the desired recurvature result is not without its side effects on nearby or adjacent corneal tissue; for example, front-surface moisture is lost, not only at the region of tissue ablation, but also in adjacent regions. Moreover, the skills required for correctly centered delivery of tissue-ablating radiation are not as accurate as is to be desired; and this centering problem is particularly the case when the controlled distribution of tissue-ablating radiation is achieved via an erodible mask that has been so profiled as in the course of its exposure to tissue-ablating radiation, to achieve a given recurvature of the cornea.

BRIEF STATEMENT OF THE INVENTION

It is an object of the invention to provide means whereby surgery of the character indicated may be performed with greater accuracy and precision than heretofore.

Another object is to meet the above object with reduced side effects in corneal regions near and adjacent the optically used region of the cornea.

A further object is to meet the above objects with means whereby a surgeon having less than the greatest manual dexterity and operative skills may nevertheless perform a PRK procedure with predictably greater precision and safety.

A specific object is to provide a template (a) which will flexibly conform to the curvature of the cornea, and (b) which will sufficiently adhere to the eye to aid in alleviation of above-noted difficulties.

Another object is to provide means whereby epithelium removal prior to surgery can be reliably minimized, thereby facilitating a reduction of recovery time for epithelium regrowth.

A further specific object is to achieve the above objects for the case of using an erodible mask in a PRK procedure.

The invention achieves the foregoing objects by providing a template or mask of flexible material that is so fenestrated or otherwise configured as to be self-adherent to the cornea in the region outside of and surrounding the central optically used area of tissue-ablating recurvature, the template being configured to provide ready centering on the visual axis. The self-adherence is relative, intended only to serve for correct centering, and for moisture-retention, regardless of the corneal curvature to which it is applied.

BRIEF DESCRIPTION OF THE DRAWINGS

The invention will be described in detail, for several preferred embodiments, in conjunction with the accompanying drawings, in which.

DETAILED DESCRIPTION

The invention will be initially described in connection with the different but generally circular embodiments of FIGS. 1 and 2, each of which is suitably formed from initially flat sheet material in the nature of a haptic which must be very compliant in the axial direction, i.e., the axial direction through the center and normal to the plane of each of these embodiments. Such compliance enables either of these embodiments to be self-conforming to the surface of a cornea upon wetting contact with natural fluid at the surface of the cornea. Each of these embodiments has a central opening, defined in the case of FIG. 1 by a continuous inner edge that is circular, with a diameter $D_1$. The compliant material is suitably polyimide, collagen or gelatin of 30-micron or greater thickness.

Figure 1:
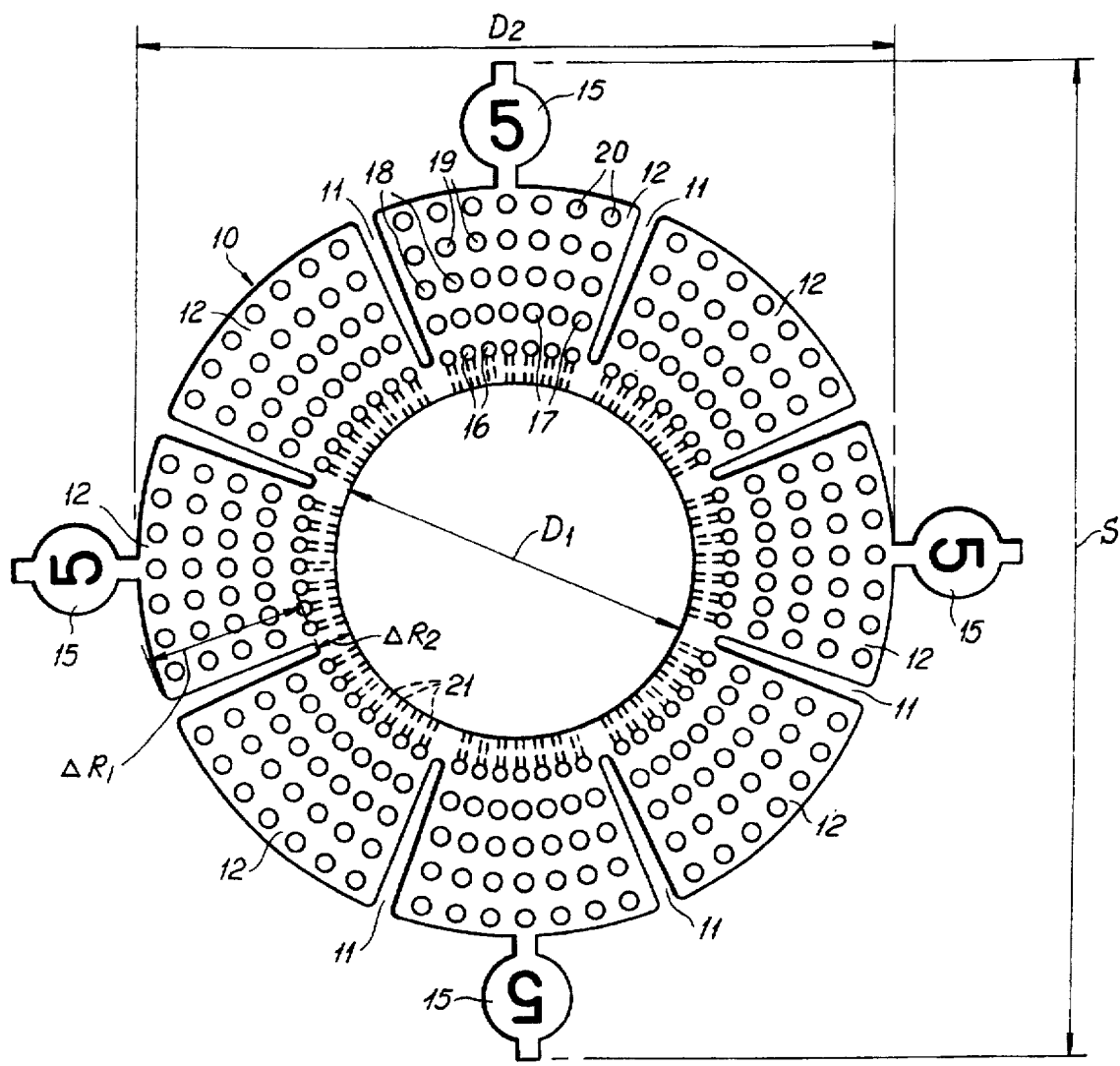
FIG. 1 is a greatly enlarged plan view of a template or mask of the invention, in its normally flat state, but available for immediate use in application to a cornea prior to performing a PRK procedure.

The template 10 of FIG. 1 has eight outwardly divergent radial slots 11 at equal spacing, thus defining eight sector-shaped radial arms or legs 12, integrally joined to a relatively narrow annulus 13 having the circumferentially continuous inner edge 14 of diameter $D_1$. The slots 11 are typically of radial extent $\Delta R_1$ approximately four times the radial width $\Delta R_2$ of the relatively narrow inner annulus 13. The inner diameter $D_1$ is typically 4.0, 5.0 or 6.0-mm, depending upon the surgeon's decision as to how large an area of PRK sculpting (i.e., recurvature) surgery is to be performed for a particular patient. In the form shown, the diameter $D_1$ is 5-mm and is so indicated by an inscribed or otherwise marked outward tab 15, at pairs of diametrically opposed locations which are 90 degrees apart; the outer diameter $D_2$ is typically 10 to 16-mm, and the total span S between outer limits of diametrically opposite tabs 15 is typically 20-mm, so that at least two of the tabs 15 can be manipulated beneath the patient's lids, for lid retention of the applied template. These tabs 15 may serve to numerically indicate the size of the central opening; they also are convenient points for tweezer engagement to and manipulated positioning of template 10 on a patient's cornea.

Although it is not necessary that the template 10 be black or opaque, it is desirable that its pigmentation be sufficiently dense that the inner edge can be clearly delineated for such visual and manipulative purposes as to enable the surgeon to observe concentric positioning of edge 14 with respect to the patient's iris opening, at which point the arms or legs 12 will drape or can be draped into conformance with the convex profile of the cornea. It is also of value in certain instances to metalize (as by vacuum-metalizing) the front surface of the template for reflection purposes, thereby "toughening" the material of the template and retarding its erodability, thus providing greater assurance that irradiation exposure will be limited only to the areas predetermined for ablation.

It is a feature of the invention that plural openings or foraminations shall be in distributed array over each of the arms or legs 12. As shown, there are five sets of concentric circular loci over which a plurality of seven spaced openings is formed in each arm or leg 12. The inner locus of openings 16 is over such a short arc for each arm or leg 12, that the inner openings 16 must be of smaller diameter than those of surrounding loci. Typically, the openings 16 are of 200-micron diameter, while those openings 17, 18, 19, 20 of successively expanded circular loci are of 250-micron diameter.

The openings 16 to 20 for each of the arms or legs 12 are of such size as to constitute centers of capillary attraction for local entrapment of surface moisture of the cornea, whereby to better adhere each leg to the convex curvature of the cornea and thus to continuously maintain the attachment of template 10 throughout a PRK procedure that is operative within the inner edge 14. The openings 16 to 20 also serve for retention of water or saline solution for hydration of an outer annulus of the cornea during the course of a cornea-sculpturing procedure on the central circular area of the cornea.

The inner edge 14 performs the additional function of safely delineating the central area over which epithelium should be removed prior to commencement of laser-sculpting surgery. The inner edge 14 thus forms, with the resulting margin of epithelium removal, a dam for accumulation of liquid, and shallow radial grooves 21 on the underside of the template 10, provide individual passages from the dam to the respective openings 16, whereby to utilize capillary attraction to draw off moisture from the dam to the respective openings 16.

Figure 2:
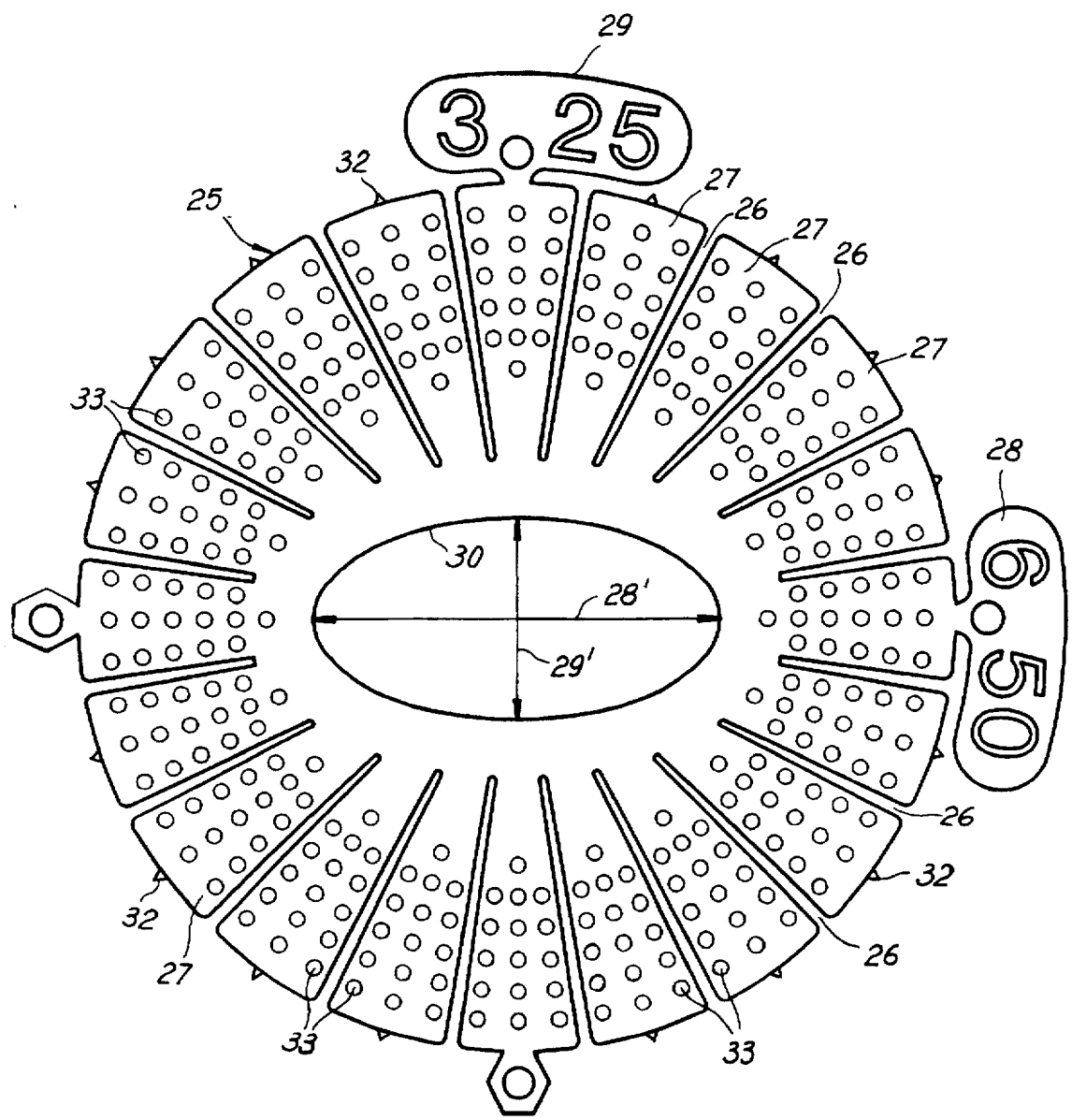
FIG. 2 is a similar view of a modification having particular application to PRK use in conjunction with a procedure to reduce diagnosed astigmatism condition.

The template 25 of FIG. 2 generally resembles the template 10 of FIG. 1, but it is specific to control of a corneal sculpture to effect correction for a diagnosed astigmatic condition. To this end, the central opening 30 of template 25 is oval or generally elliptical, and legends on quadrature tabs 28, 29 identify the respective major and minor dimensions of the opening 30. In the particular case of FIG. 2, therefore, the legend "6.50" on tab 28 tells the surgeon that the elongate extent of opening 30 on major dimension 28' is 6.50 mm, and the legend "3.25" on tab 29 advises that the transverse extent of opening 30 on minor dimension 29' is 3.25 mm.

As is the case of FIG. 1, the template 25 of FIG. 2 is provided with plural radially outward slots 26 between flexible arm members 27. The arm members are shown as 20 in number, thus making it possible for the surgeon to judge angle or angle displacement merely by counting off the number of arm members 27, and hence the number of 18-degree increments, from one location of his chosen reference, to another location at which he intends particularly oriented reference for his astigmatism-correcting surgery.

In view of the oval nature of the opening 30, FIG. 2 illustrates that the slots 26 between arms 27 may be of varying radial depth, to the end that all slots terminate at essentially the same radial offset Δ from the perimeter of opening 30, thus rendering the template more flexibly drapable in conformance with a patient's corneal curvature.

As also in the case of FIG. 1, the template 25 is provided with patterns of fenestrating apertures 33 that are sized to draw and retain moisture at the surface of the eye, and the inner margin 30 determines an outer limit of epithelium removal prior to surgery. And by providing each arm element 27 with a central pointer 32, the surgeon is able to judge his angular orientations within estimated and more finely divided fractions of the 18-degree increments; also, with microscope viewing through a reticle, the pointers 32 enable enhanced precision of angle interpretation.

Figure 3:
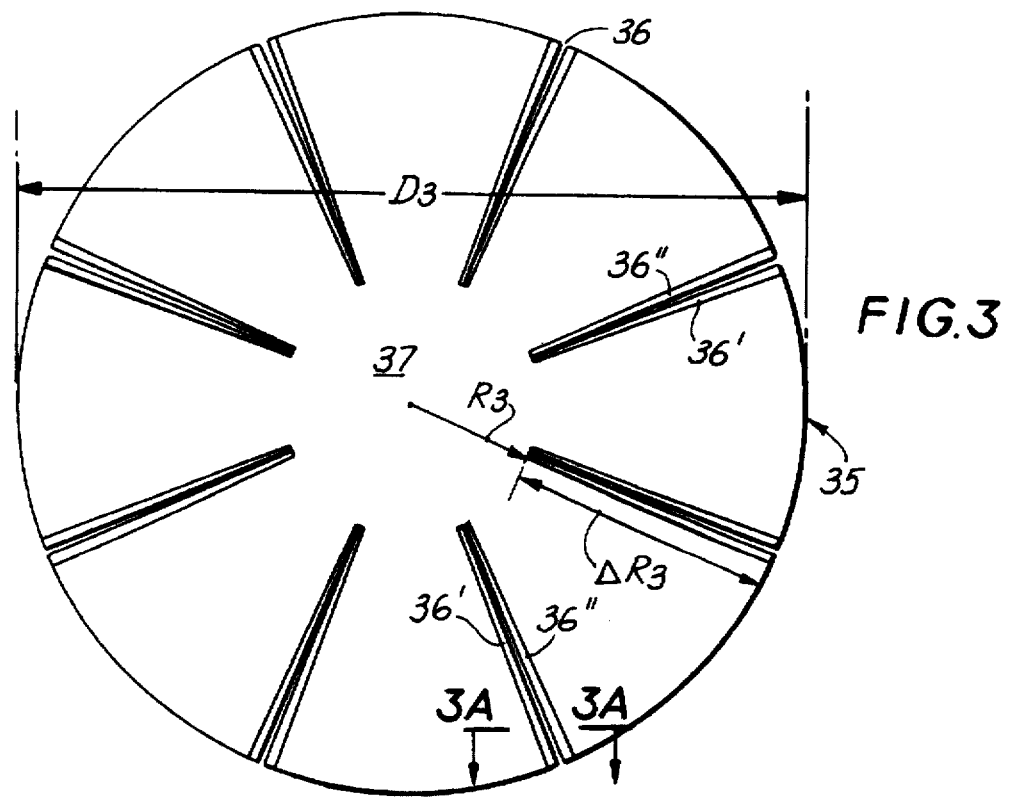
FIG. 3 is a plan view of an erodible mask for use with the structure of FIG. 1.

FIG. 3 illustrates an erodible mask 35 which has a built-in feature of self-adaptation to the convex curvature of the cornea to which it may be applied for PRK-recurvature purposes. This mask is shown to be circular, preferably of outside diameter $D_3$ to fit within and be located by the inner rim 14 (30) of described template of FIG. 1. $D_3$ may thus be in such slight excess of $D_1$ of FIG. 1 as to reduce to $D_1$ in self-adaptation to the convex curvature of the patient's cornea.

Figure 3A:
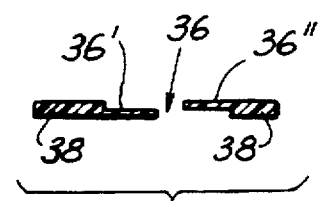
FIG. 3A is a sectional view taken at 3A—3A in FIG. 3.

For self-adaptation to such convex curvature, mask 35 is shown with plural equally spaced radially outwardly expanding slot formations 36, here shown as eight slots, extending for a radial extent $\Delta R_3$ which is approximately twice the radius of an unslotted central region 37. Thus, if $D_3$ is close to 6-mm, the unslotted region 37 is of radius $R_3$ of about 2-mm, and the length $\Delta R_3$ of slots 36 is about 4-mm. FIG. 3A illustrates on an enlarged scale that flexible arms or tabs 38 defined by slots 36 have adjacent, suitably milled formations 36', 36" such that a draped self-adaptation to the cornea will bring formations 36', 36" into overlap, with a combined thickness equal to the basic thickness of mask 35. The erodible material of mask 35 may be polyimide, collagen or gelatine, with 30 or more micron thickness.

Figure 5:
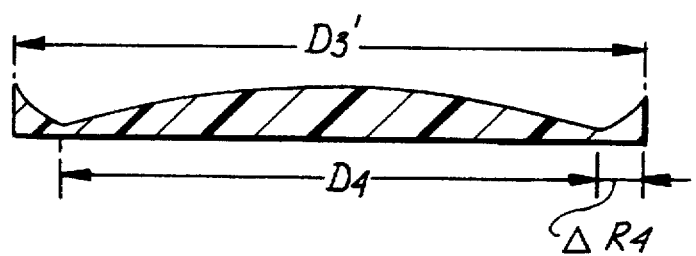
FIG. 5 is a similarly enlarged sectional view of a diametrical profile for use in the mask of FIG. 3, for hyperopia reduction.
Figure 4:
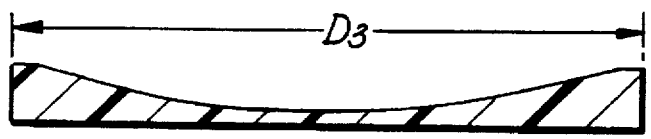
FIG. 4 is an enlarged sectional view of a diametrical profile for use in the mask of FIG. 3, for myopia reduction.

The diametrical section profile of mask 35 is seen in FIG. 4 to be concave for purposes of PRK development of a myopia-correcting reduction in curvature of the cornea. Similarly, in FIG. 5 the sectional profile is seen to be convex for PRK development of a hyperopia-correcting increase in curvature of the cornea, for a diameter $D_4$. In the latter connection, it is noted that the erodible profile, throughout an outer circular annulus of extent $\Delta R_4$, is of progressively increasing thickness, to avoid creation of a sharp circular edge in the cornea at the outer limit of a hyperopia-correcting procedure.

In further connection with FIG. 4, the indicated profile for myopia reduction is of course the same profile regardless of the diametrical plane in which the section is taken. On the other hand, if the profile of FIG. 4 is taken to characterize a section taken in a fixed diametrical plane which is normal to an axis in which cylindrical curvature is to be reduced, then FIG. 4 is illustrative for an erodible mask to produce an astigmatism-reducing PRK development.

In use of a template of the invention, care must be taken that the template is centered on the optical center of the patient's eye. Once thus applied and draped in conformance with the patient's eye curvature, the described capillary and wetting actions stabilize and retain the centering, which can be further aided by application of a sponge material at the outer periphery of the template. With such assurance of template fixation, the surgeon is able to watch the ablated region more carefully, should there be any eye movement, calling for the surgeon's prompt adoption of a suitable corrective measure.

What is claimed is:

1. As an article of manufacture adapted for self-adherent removable mounting to the cornea of an eye and in aid of a photorefractory keratectomy procedure wherein a predetermined optically used central circular area of the cornea is subjected to a predetermined distribution of tissue-ablating radiation, an annular corneal drape of uniformly thin initially flat flexible sheet material having a circumferentially continuous inner edge defining a central circular opening of at least the diameter of said central circular area, having a radial extent between inner and outer radii, said drape having an outer circular periphery interrupted by a plurality of radial slits at angular spacings, said slits being of radial length which is at least half said radial extent, thereby defining flexible radial legs, said legs having patterns of spaced openings, said openings being sized for retention of a liquid for hydration of an outer annulus of the cornea during the course of a cornea-sculpturing operative procedure on the central circular area of the cornea.

2. The article of claim 1, in which said patterns of spaced openings include a first circular locus for a first series of said openings at radially outward offset from said inner edge, and said drape having for each of the openings of said first series and within said offset at least one radial groove in one circumferentially continuous surface of said drape, each said groove extending from said inner edge to one of said first series openings, whereby to induce capillary flow of moisture away from said central area and to areas of moisture accumulation at the openings of said first series.

3. The article of claim 1, in which the plurality of radial slits is eight, thereby to define eight flexible legs, said openings being in angularly distributed plurality in each of said legs and on each of a plurality of radially spaced circular loci.

4. The article of claim 1, in which for each of said flexible legs said openings comprise a set of openings at equal radial spacing and on a single radial alignment.

5. The article of claim 1, in which at least two of said legs extend in diametrically opposite directions, each of said two legs having integrally formed therewith a radially outward tab extension for enhanced maneuverability into a centered and angularly oriented application of said drape to an eye.

6. The article of claim 1, in combination with an erodible mask of circular configuration and adapted for centrally stabilized reference to the central opening of said drape, said erodible mask having a precharacterized variation of thickness such that upon exposure of an eye to tissue ablating radiation via said mask, a precharacterized recurvature of the cornea may be achieved within said central area.

7. The article and combination of claim 6, wherein said mask includes an outer circumferentially continuous edge that is sized to fit in and to the inner edge of said central opening.

8. The article of claim 1, in which an angular midpoint outer indicium is an integral formation of a plurality of said legs.

9. The article of claim 1, in which at least one surface of said drape has a metallic coating.

10. The article of claim 1, in which said flexible sheet material is sufficiently pigmented that said inner edge can be clearly delineated for such visual and manipulative purposes as to enable a surgeon to observe concentric positioning of said edge, with respect to a patient's iris opening.

11. A kit for use in photorefractive keratectomy of a predetermined optically used central circular area of the anterior surface of a cornea, said kit comprising:

an annular corneal drape of flexible sheet material having a circumferentially continuous inner edge defining a central circular opening of an least the diameter of said central circular area, said drape having an outer periphery interrupted by plural radially spaced radial slits at equal angular spacings; and an erodible mask of circular configuration and adapted for centrally stabilized reference to the central opening of said drape, said erodible mask having a precharacterized variation of thickness such that upon exposure of an eye to tissue-ablating radiation via said mask, a precharacterized recurvature of the cornea may be achieved within and limited to said central area.

12. The kit of claim 9, wherein said mask having an outer circular edge that is interrupted by radial slits having radially divergent side edges, whereby to define spaced flexible legs which draw into closer adjacency in draped adaptation to convex curvature at the front surface of a cornea.

13. The kit of claim 12, in which each radial slit defines a pair of adjacent slit-defining radial edges of said mask, one edge of each pair is locally reduced to substantially half thickness along one surface of the mask, and the other edge of each pair is locally reduced to substantially half thickness along the opposite surface of the mask, whereby upon draped application to the convex curvature of a cornea, a draped conformance to corneal curvature may be achieved with a lapped relation of half-thickness reductions at each pair of slit-defining radial edges.

14. The kit of claim 12, in which the radial length of the slits of said mask is at least one half the radial extent of said mask.

15. The kit of claim 12, in which the radial length of the slits of said mask is at least no greater than substantially two-thirds of the radial extent of said mask.

16. The kit of claim 12, in which the said precharacterized variation of mask thickness is such as to achieve a myopia correction upon exposure to tissue-ablating radiation.

17. The kit of claim 12, in which the said precharacterized variation of mask thickness is such as to achieve a hyperopia correction upon exposure to tissue-ablating radiation.

18. The kit of claim 12, in which the said precharacterized variation of mask thickness is such as to achieve an astigmatic correction upon exposure to tissue-ablating radiation.

19. As an article of manufacture adapted for self-adherent removable mounting to the cornea of an eye and in aid of a photorefractory keratectomy procedure wherein a predetermined optically used central circular area of the cornea is subjected to a predetermined distribution of tissue-ablating radiation, an annular corneal drape of flexible sheet material having a circumferentially continuous inner edge defining a central generally oval opening having a maximum dimension which is at least the diameter of said central circular area, said drape having an outer circular periphery interrupted by an even number of radial slits at equal angular spacings, thereby defining flexible radial legs, said maximum dimension being aligned with two of said legs which are diametrically opposed.

20. The article of claim 19, in which one of said two legs has integrally formed therewith a radially outward tab extension with an inscribed numerical indicium of said maximum dimension.

21. The article of claim 20, in which the number of legs is a multiple of four, and said central generally oval opening has a minimum dimension which is aligned with another two diametrically opposed legs, one of said other two diametrically opposed legs having integrally formed therewith a radially outward tab extension with an inscribed numerical indicium of said minimum dimension.

22. The article of claim 19, in which said legs have patterns of spaced openings in said legs, said openings being sized for retention of liquid for hydration of an outer annulus of the cornea during the course of a cornea-sculpturing operative procedure on the central circular area of the cornea.

23. The article of claim 19, in which each of said radial slits is of a radial length that is short of intercept with said generally oval opening, said radial length being so determined as to provide for each slit a radially inner limit at radial offset from said opening, said radial offset being substantially the same for all of said slits.

24. As an article of manufacture adapted for self-adherent removable mounting to the cornea of an eye and in aid of a photorefractory keratectomy procedure wherein a predetermined optically used central circular area of the cornea is subjected to a predetermined distribution of tissue-ablating radiation, an annular corneal drape of uniformly thin initially flat flexible sheet material having a circumferentially continuous inner edge defining a central generally oval opening having a maximum dimension which is at least the diameter of said central circular area, the annulus of said drape having a radial extent between inner and outer radii, said drape having an outer circular periphery interrupted by a plurality of radial slits at angular spacings, said slits being of radial length which is at least half said radial extent, thereby defining flexible radial legs, said legs having patterns of spaced openings, said openings being sized for retention of a liquid for hydration of an outer annulus of the cornea during the course of a cornea-sculpturing operative procedure on the central circular area of the cornea.

25. The article of claim 23, in which said maximum dimension is aligned with two of said legs which are diametrically opposed.

* * * * *